US008256086B2

(12) United States Patent
Shutler et al.

(10) Patent No.: US 8,256,086 B2
(45) Date of Patent: Sep. 4, 2012

(54) METHOD OF PRODUCING MISSILE NOSE CONES

(75) Inventors: Robert A. Shutler, Mogadore, OH (US); Margaret Rose Manning, Akron, OH (US); Paul A. Leitch, Brecksville, OH (US); Paul E. Liggett, Wooster, OH (US)

(73) Assignee: Lockheed Martin Corporation, Bethesda, MD (US)

( * ) Notice: Subject to any disclaimer, the term of this patent is extended or adjusted under 35 U.S.C. 154(b) by 741 days.

(21) Appl. No.: 12/491,953

(22) Filed: Jun. 25, 2009

(65) Prior Publication Data

US 2010/0326182 A1    Dec. 30, 2010

(51) Int. Cl.
*B23Q 17/00* (2006.01)
(52) U.S. Cl. ........... 29/407.1; 29/890.01; 29/407.05; 29/407.09; 102/374; 102/379; 102/293; 86/51; 86/1.1; 702/42; 702/43; 73/37; 73/167; 73/802; 73/838
(58) Field of Classification Search ........... 29/407.1, 29/890.01, 407.09, 407.05; 102/374, 379, 102/293, 387; 702/43, 42, 35, 81, 182, 185; 73/37, 167, 802, 838; 86/51, 1.1
See application file for complete search history.

(56) References Cited

U.S. PATENT DOCUMENTS

| 2,889,772 | A | * | 6/1959 | Howard | 102/390 |
| 3,110,262 | A | * | 11/1963 | West | 102/399 |
| 3,279,405 | A | * | 10/1966 | Billmeyer | 114/20.1 |
| 3,477,376 | A | * | 11/1969 | Blatt et al. | 102/399 |
| 3,944,118 | A | * | 3/1976 | Trill | 222/134 |
| 4,149,404 | A | * | 4/1979 | White | 73/49.7 |
| 4,788,914 | A | * | 12/1988 | Frater | 102/399 |
| 4,793,179 | A | * | 12/1988 | Carlson | 73/167 |
| 4,900,848 | A | * | 2/1990 | Saito et al. | 549/517 |
| 5,235,128 | A | * | 8/1993 | Hardesty et al. | 102/351 |
| 5,438,878 | A | * | 8/1995 | Carroll, Jr. | 73/788 |
| 6,732,057 | B2 | * | 5/2004 | Hamad | 702/42 |
| 6,883,367 | B2 | * | 4/2005 | Feng et al. | 73/81 |
| 6,983,658 | B2 | * | 1/2006 | Wenski | 73/800 |
| 7,010,435 | B2 | * | 3/2006 | Pourcelot et al. | 702/43 |
| 7,039,528 | B2 | * | 5/2006 | Gao et al. | 702/35 |

(Continued)

OTHER PUBLICATIONS

Lockheed Martin; *Vertical Launch Antisubmarine Missile (VLA)—Protecting the Fleet Against Submarine Attack*; vol. VLA_0507, 2007—(the year of publication is sufficiently earlier than the effective U.S. filing date so that the particular month of publication is not in issue).

*Primary Examiner* — Jermie Cozart
*Assistant Examiner* — Bayan Salone
(74) *Attorney, Agent, or Firm* — Renner Kenner Greive Bobak Taylor & Weber

(57) ABSTRACT

A method for producing a missile nose cone is disclosed. The method consists of manufacturing a first missile nose cone from a first lot of polymeric material and determining a first rupture value. The method further consists of manufacturing a second missile nose cone from a second lot of polymeric material and determining a second rupture value of the second missile nose cone. Both first and second lots of material are mixed into a test batch with one another based on their associated rupture values. An evaluation missile nose cone is then manufactured from the test batch and a determination is made as to whether the evaluation missile nose cone has a desired rupture value. If a desired rupture value is not obtained, then the mixing and evaluation steps are repeated.

9 Claims, 4 Drawing Sheets

U.S. PATENT DOCUMENTS

| | | | |
|---|---|---|---|
| 7,470,103 B2 * | 12/2008 | Tisenchek et al. | 415/1 |
| 7,546,224 B2 * | 6/2009 | Campbell | 703/1 |
| 7,716,239 B2 * | 5/2010 | Murez et al. | 707/779 |
| 8,015,550 B2 * | 9/2011 | Berenbach et al. | 717/124 |
| 8,175,820 B2 * | 5/2012 | Hatanaka et al. | 702/39 |
| 2003/0200656 A1 * | 10/2003 | Wilson | 29/890.01 |
| 2008/0262754 A1 * | 10/2008 | Oudovikine | 702/42 |
| 2010/0294113 A1 * | 11/2010 | McPherson | 86/1.1 |

* cited by examiner

METHOD OF PRODUCING MISSILE NOSE CONES

TECHNICAL FIELD

The present invention relates to the development of a missile nose cone meeting material and performance specifications. More particularly, the present invention relates to a methodology that produces a missile nose cone possessing material characteristics to ensure proper launch and flight of the missile and bursting of the nose cone as the missile impacts water.

BACKGROUND

Anti-submarine missiles, which carry a torpedo payload, are effective deterrents in defending a ship or a fleet of ships. In most embodiments, the missile is maintained in a vertically-oriented canister maintained on a ship. In other embodiments, the missile may be launched from an aircraft. After launch, the missile travels to a target area where a parachute deploys. At water entry, the missile deploys the torpedo to search for the submarine target. Critical to operation of the missile and the torpedo is the missile's nose cone. The nose cone needs to be rigid enough to pierce a membrane that covers the canister and withstand the rigors of flight, but the nose cone also needs to shatter at water entry to allow for proper deployment of the missile. Moreover, the nose cone needs to shatter in small enough pieces so that they do not damage the torpedo's tail fins.

In the development of the missile nose cone, selection of the nose cone material is extremely important to meet all desired operational characteristics when considering the sensitivity of the nose cone and its role in protecting the missile during flight. Any material that does not meet the required characteristics can lead to a misguided or damaged missile resulting in a defeated mission.

The current art methodology for producing missile nose cones includes purchasing polymeric material from a manufacturer, molding the nose cone, and then hoping the finished nose cone meets desired requirements. Due to the precision needed for the material used to make the missile nose cone, many problems result from the current methodology.

The first problem stems from the cone's manufacturing process which relies on use of a polymeric material that exhibits a broad range of properties related to its parent manufacturing processes. If the material's properties are not adequately controlled at the material manufacturing locations, the missile nose cone will not perform as desired. Many times, material within each purchased lot is above or below the operational strength range for the missile nose cone. This is due to process variability such as time, temperature, human intervention, and ingredient variability. Secondly, large lots are the only means of purchasing the nose cone material. As a result, if the lots do not meet specifications, the material purchased cannot be utilized, wasting time, resources and money.

Therefore, there is a need in the art for a method that alleviates the effects of process variability in the manufacture of missile nose cones, allows material to be used in the nose cones to be produced predictably without total reliance on the material manufacturer, and that meets the precise material requirements of the missile nose cone. Accordingly, there is a need for missile nose cones to be manufactured to specific end-use properties. And there is a need for formulation of specific material preparation to meet molded component performance requirements.

SUMMARY OF THE INVENTION

In light of the foregoing, it is a first aspect of the present invention to provide a method of producing missile nose cones.

It is another aspect of the present invention to provide a method for producing a missile nose cone, comprising manufacturing a first missile nose cone from a first lot of polymeric material and determining a first rupture value of said first missile nose cone, manufacturing a second missile nose cone from a second lot of polymeric material and determining a second rupture value of said second missile nose cone, mixing into a test batch said first and second lots of material with one another based upon said rupture values, manufacturing an evaluation missile nose cone from said test batch, and determining whether said evaluation missile nose cone has a desired rupture value.

BRIEF DESCRIPTION OF THE DRAWINGS

This and other features and advantages of the present invention will become better understood with regard to the following description, appended claims, and accompanying drawings wherein:

BEST MODE FOR CARRYING OUT THE INVENTION

Figure 1:
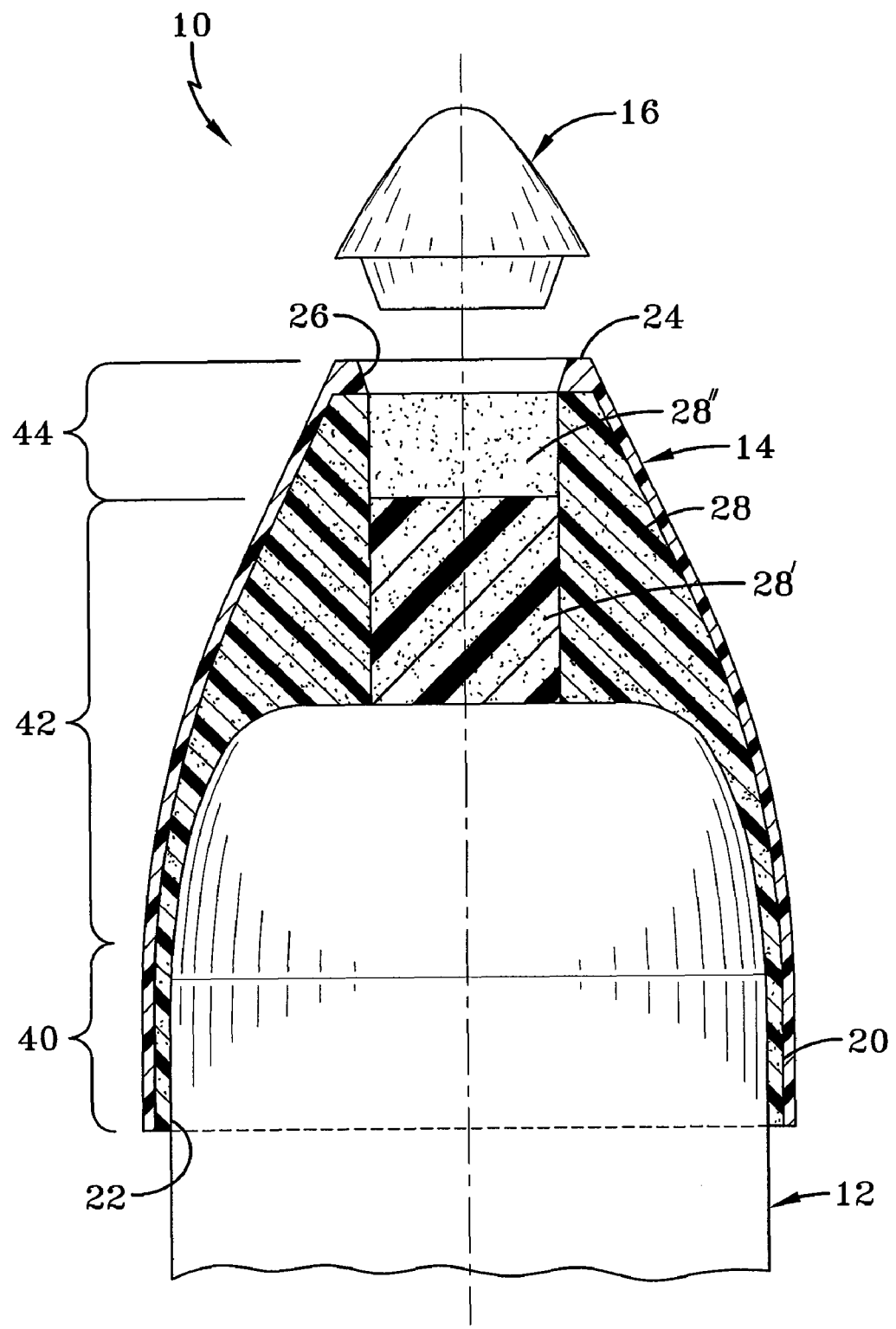
FIG. 1 is an elevational view, partially broken away and in cross-section, of the forward end of a missile showing elements of an attached nose cone in accordance with the present invention.

Referring now to the drawings, and particularly to FIG. 1, it can be seen that an upper portion of a missile is designated generally by the numeral 10. The missile includes a torpedo 12 which is deployed after the missile has completed its flight path and entered the water. As those skilled in the art will appreciate, and as described in the background of the present invention, the missile 10 is deployed from either a ship or an aircraft and flies a prescribed distance until a target area is reached. A parachute (not shown) is then deployed to slow the flight of the missile, whereupon impacting the water the torpedo 12 is deployed. The missile 10 includes a nose cone 14 which carries a separable nose cap portion 16.

The nose cone 14 includes a base end 20 that is fitted upon the torpedo 12. Specifically, the base end 20 includes a base opening 22 which is sized to receive an end of the torpedo 12. The nose cone also includes a tip end 24 opposite the base end and which has a bore opening 26 which receives the separable tip portion 16. Internal foam pieces 28, 28' and 28" are fitted within the nose cone so as to cushion and prevent damage to the forward end of the torpedo 12.

For reference, the nose cone 14 can be segmented into different portions such as a hoop section 40 at the base end 20.

Extending from the hoop section 40 is a transition section 42 wherein the nose cone further extends into a tip section 44 which receives the nose cap portion 16. The hoop section 40, the transition section 42, and the tip section 44 are configured so as to provide for full uniform aerodynamic flight of the missile 10.

As noted in the background and as fully discussed in U.S. Pat. No. 4,788,914, which is incorporated herein by reference, the nose cap portion 16 is secured to the nose cone 14 in such a manner as to facilitate operation of the missile. Briefly, at launch, the separable tip portion 16 pierces a membrane that encloses the missile during storage. Two safety pins are withdrawn from the bore opening 26 as the separable tip portion 16 passes through the membrane. However, those skilled in the art will appreciate that the nose cap portion does not fall away from the nose cone until a parachute attached at the opposite end is deployed from the missile 10. At that time, the separable tip portion 16, because of its significant weight and because of its minimal securement to the nose cone 14, falls away from the missile 10. As the missile 10 falls toward the water, the nose cone strikes the water first and the water enters the bore opening 26. The impact results in the nose cone shattering whereupon the torpedo's control system activates and directs the torpedo toward the target area.

Figure 2:
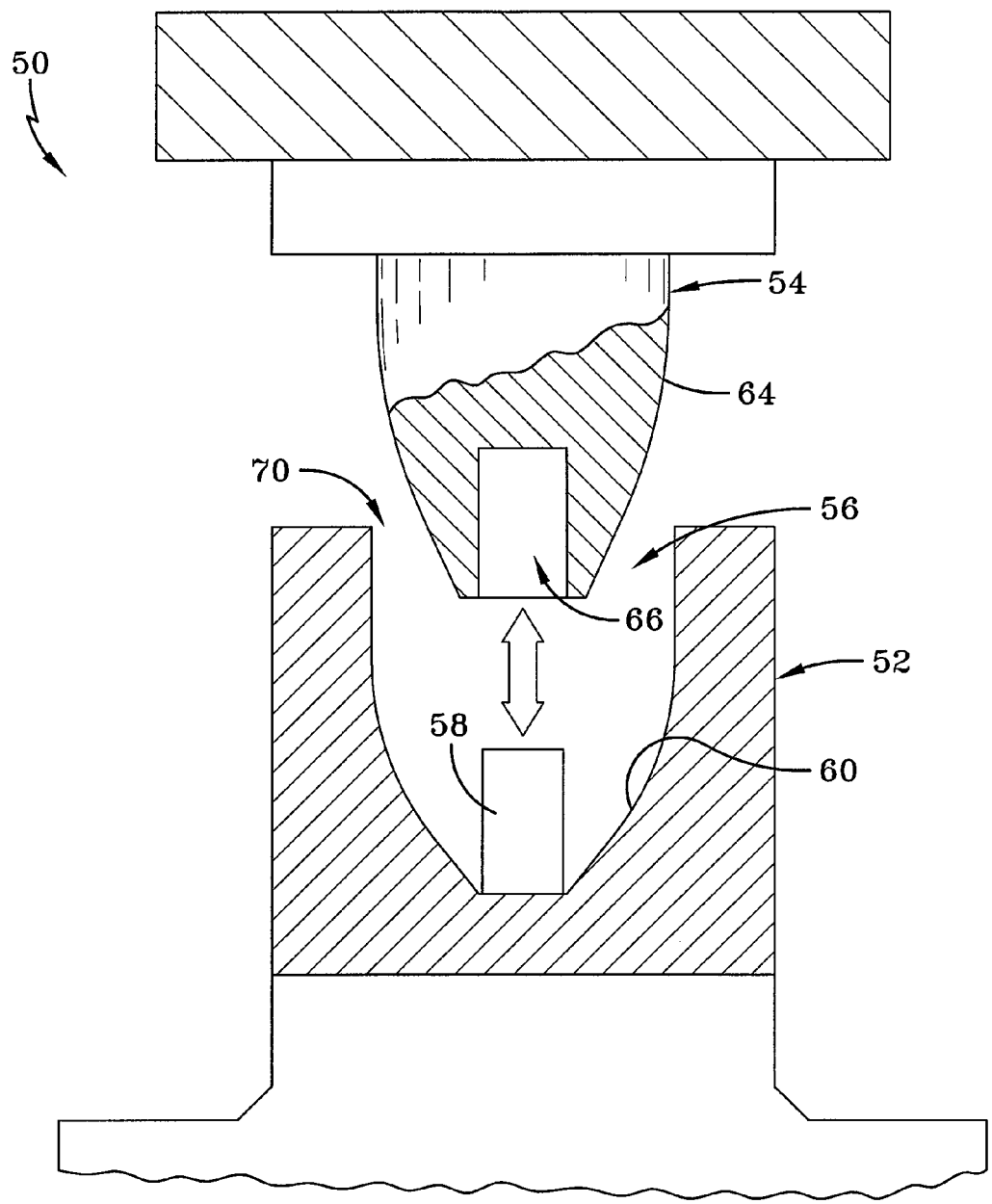
FIG. 2 is an elevational view, partially broken away and in cross-section, of a mold used to fabricate a missile nose cone according to the present invention.

To ensure proper operation of the missile and in particular the shattering of the nose cone so that it breaks away from the missile and shatters in small enough pieces so that the pieces do not damage the torpedo's propellers or fins, the method and materials used for construction of the nose cone are critical. Accordingly, referring now to FIG. 2, it can be seen that a nose cone mold is designated generally by the numeral 50. The mold 50 includes an exterior mold 52 and an interior mold 54. The exterior mold 52, which is typically supported by some type of base received in a hydraulic press, includes a cavity 56 which has an axially-extending upwardly directed alignment pin 58 at the bottom thereof. The mold 52 forms or includes an exterior cone surface 60 which forms the exterior surface of the nose cone 14. Applicable to this invention, nose cones may be formed by compression, injection and transfer molding processes or combinations of these processes.

The interior mold 54, which is carried by some type of plunger device maintained by the hydraulic press in which the mold 50 is carried, provides an interior cone surface 64 and an axially-configured, centrally disposed alignment pin receptor 66 which mates with the alignment pin 58 when the molds halves 52 and 54 are brought together.

Formed between the separated exterior mold 52 and the interior mold 54 is a gap 70. It will be appreciated that the mold halves are brought partially together in such a manner so that the alignment pin receptor 66 is received by the alignment pin 58. At that time, molding material is disposed into the gap 70 via an appropriate fixture or fixtures, such as a funnel, so that the molding material is evenly distributed between the interior and exterior molds. Prior to placing the material in the mold 50, it will be appreciated that the molds 52 and/or 54 may be preheated to temperatures of about 300° F., depending upon the particular materials selected. Additionally, the material may be preheated for a predetermined period of time before insertion into the molding halves. A shot size or appropriate amount of material is selected and loaded in between the molds and the molds are closed within a period of time, such as 120 seconds, and with a predetermined amount of pressure. Once the molds are fully brought together, they may be kept in a closed condition for a predetermined period of time, such as for 45 minutes, at a predetermined temperature, such as 300° F., so as to allow the molding material to cure. Simultaneously, the mold may be cooled by water or other fluid so as to allow the molding material to properly set and take shape. The mold may then be opened and the part removed for final processing and inspection.

Figure 3:
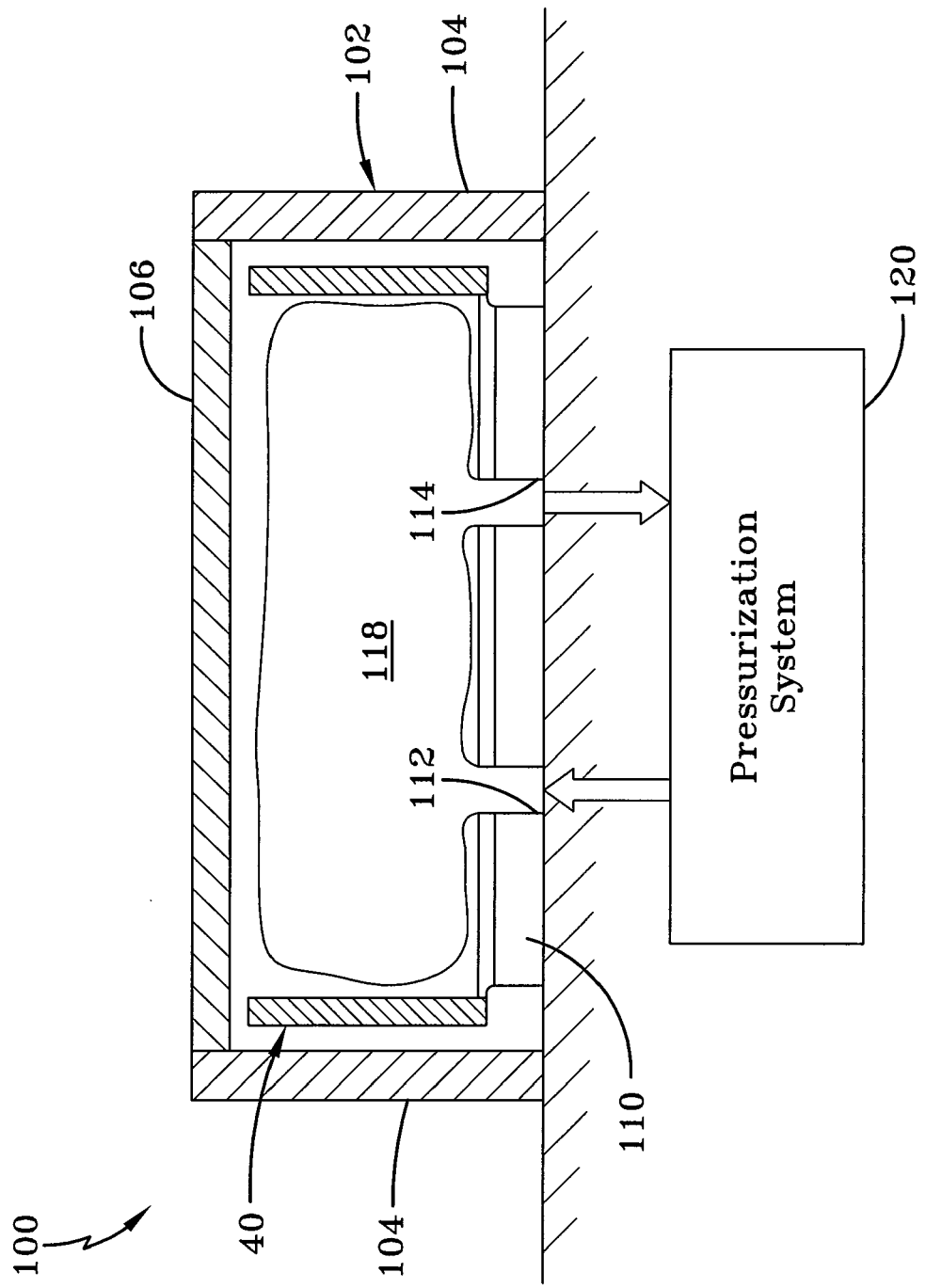
FIG. 3 is a schematic diagram, in partial cross-section, of a test fixture used to analyze a hoop section of a missile nose cone according to the present invention.

In order to determine whether the nose cone meets the precise requirements for shattering upon impact of the torpedo with the water, a testing evaluation method has been developed that fairly accurately predicts whether the nose cone will perform as needed. In order to test the nose cone, the hoop section 40 is cut from the remainder of the nose cone 14 and evaluated in a testing device. Specifically, as can be seen in FIG. 3, a test fixture is designated generally by the numeral 100. The test fixture 100 includes a containment system 102 which includes a circular side wall 104 which is slightly larger than the outer diameter of the hoop section 40. A removable top plate 106 is securable to the side walls 104. A bottom plate 110 is carried by a surface upon which the side walls are also supported. The bottom plate 110 includes an inlet port 112 and an outlet port 114 extending therethrough. A bladder 118 is received within the containment system 102 and is configured in such a manner so that it is detachably connected with the ports 112 and 114. A pressurization system 120, which may utilize a fluid such as water or other hydraulic-type material, is connected to the bladder 118 through the ports 112 and 114.

The hoop section 40 is disposed within the side walls 104 such that the bladder, in an unfilled condition, is received within the interior of the hoop section. The containment system 102 is closed, whereupon the pressurization system 120 is activated so as to fill the bladder 118 such that it contacts the interior surfaces of the hoop section 40. The pressurization system continually fills the bladder until such time that the hoop section ruptures or breaks. The value at which the hoop section "ruptures" is then recorded for further evaluation.

Based upon the information collected from the results of testing the hoop sections and the type of material used to form the nose cone, a determination can be made as to whether the material used in the manufacture of the nose cone is suitable for use. It will be appreciated that in some instances, if the rupture value is too high, the nose cone would not shatter upon entering the water and would defeat operation of the torpedo. In other instances, if the nose cone material has a low rupture value, the nose cone might break upon impact with the missile canister membrane or during flight. Alternatively, if the rupture value is too low, the material could be so weak that when the nose cone does break, it breaks into large sections which could damage the propeller of the missile and further defeat the operation thereof. Accordingly, it is desirable to have a rupture or breakage value of the nose cone material which is optimal for performance of the missile and the torpedo.

Figure 4:
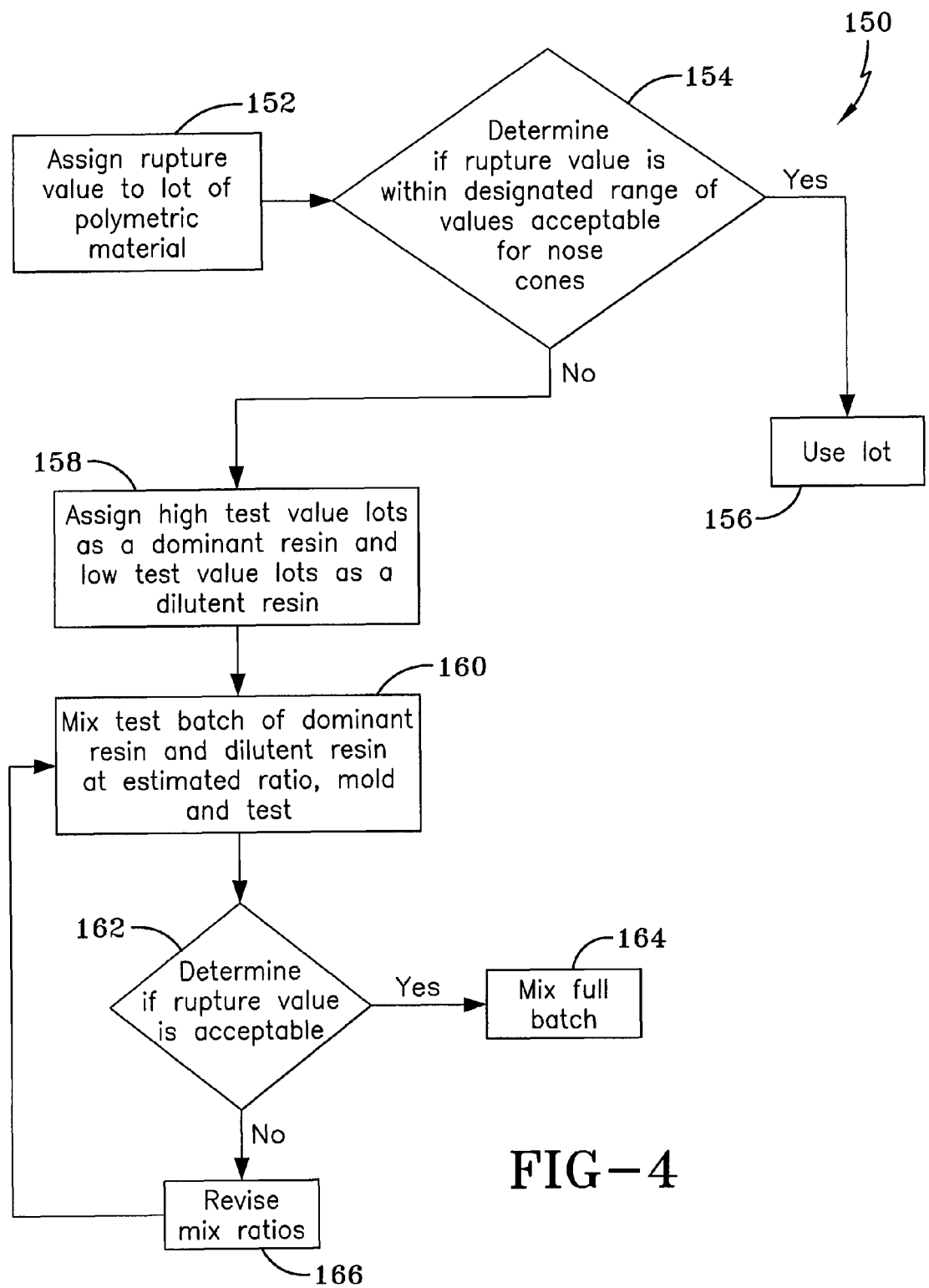
FIG. 4 is a flow chart showing the methodology for determining a mix ratio of dominant resin and dilutent resin for use in manufacturing the missile nose cone.

Referring now to FIG. 4, a methodology for determining whether a nose cone material meets the required operational values is designated generally by the numeral 150. At step 152 a rupture value is determined by the methodology described above and assigned to a lot of polymeric material that is used to form the nose cone 14. At step 154 it is determined whether the rupture value is within a designated range of values acceptable for operation of the nose cone as described above. If the rupture value is within range, then at step 156 that particular lot of polymeric material is used for manufacture of the nose cones. However, if at step 154 the determined rupture value is not within the desired range, then the process proceeds to step 158 where a high test value results in that particular lot being designated as a dominant resin. Alternatively, if it is determined that a rupture value is too low at step 154 for a particular lot, then the lot is designated as a dilutent resin. In other words, if a particular lot of material has a value higher than the desired range, it is considered to be a harder material than required and is designated as a dominant resin, while lots with a lower than desired rupture value are designated as a dilutent resin. Based upon the assigned values, a test batch is mixed at 160 with the dominant resin and dilutent resin at an estimated ratio, whereupon the mixed batch of material is molded as shown and described in relation to FIG. 2 and tested as shown and described in relation to FIG. 3. It will be appreciated that if the material has a particularly high test value in regard to when it ruptures, that it is considered to be a strong material and, as such, it would only need to constitute a small value or ratio of the test batch, whereas a very low value of dilutent resin could be mixed with a very high value of dominant resin so as to obtain the desired rupture for a lot of polymeric material. In other words, the ratio amounts of the dominant and dilutent resins can be selected based on a particular resin's rupture value associated with a manufacture of a nose cone. Accordingly, at step 162 after the test batch has been mixed, molded and tested, a rupture value is determined to see whether it falls within an acceptable range. If this is the case, then a full batch is mixed according to the ratios determined at the test batch step, at step 164. However, if the determined rupture value for the test batch does not meet the desired rupture value, then at step 166 the mix ratios are revised for the dominant and dilutent resins and the steps 160 and 162 are repeated until a desired value is obtained.

Based upon the foregoing, it will be appreciated that a methodology has been developed that results in generation of a nose cone which has the desired rupture values and which ensures proper operation of the missile and torpedo. Such a methodology avoids conditions of process variability in the manufacture of the polymeric material and where that material is molded to a desired shape. This alleviates the effects of process variability as a result of typical material manufacturing processes where external factors such as, but not limited to, time, temperature, human intervention and ingredient variability create variable end-use performance which is not acceptable. The present invention solves this problem by providing a desired product performance by reducing the effects mentioned above.

The methodology of the present invention is further advantageous in that it allows for mixing of different resin lots together in a calculable and predictable manner wherein the final product performance is directly related to the concentration of the dilutent resin and the dominant resin as opposed to variable external effects of material and processing.

Still another advantage of the present invention is that the variable conditions of the material and process are compensated for by adjusting the concentration of the resins to achieve desired mechanical and physical properties and end-product performance. This allows for assurance of the availability of material as opposed to relying on a material manufacturer to blend specific materials to suit performance and processing. And this methodology allows for use of resin material that would otherwise be scrapped because it does not meet the required product parameters.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A method for producing a missile nose cone, comprising:
   manufacturing a first missile nose cone from a first lot of polymeric material and determining a first rupture value of said first missile nose cone;
   manufacturing a second missile nose cone from a second lot of polymeric material and determining a second rupture value of said second missile nose cone;
   mixing into a test batch said first and second lots of material with one another based upon said rupture values;
   manufacturing an evaluation missile nose cone from said test batch; and
   determining whether said evaluation missile nose cone has a desired rupture value.

2. The method according to claim 1, further comprising:
   cutting a hoop section from each said first and second missile nose cones and determining said rupture values from said hoop sections.

3. The method according to claim 2, further comprising:
   positioning said hoop sections into a test fixture which comprises a bladder received within said hoop section, wherein said bladder is expanded until said hoop section ruptures.

4. The method according to claim 1, further comprising:
   designating said lot of polymeric material with a higher comparative rupture value as a dominant resin; and
   designating said lot of polymeric material with a lower comparative rupture value as a dilutent resin.

5. The method according to claim 4, further comprising:
   selecting percentage amounts of said dominant and dilutent resins for mixing into said test batch based upon rupture values of each said lot.

6. The method according to claim 5, further comprising:
   cutting a hoop section from said evaluation missile nose cone manufactured from said test batch.

7. The method according to claim 6, further comprising:
   repeating selecting and determining steps until a desired ratio of dominant and dilutent resin obtains said desired rupture value.

8. The method according to claim 7, further comprising:
   fully mixing said first and second lots in said desired ratio; and
   manufacturing missile nose cones with said fully mixed lot.

9. The method according to claim 1, further comprising:
   designating said desired rupture value as being between two values.

* * * * *